United States Patent
Holzmayer et al.

(10) Patent No.: US 6,426,412 B1
(45) Date of Patent: Jul. 30, 2002

(54) NUCLEIC ACIDS ENCODING HUMAN IMMUNODEFICIENCY VIRUS TYPE 1 GENETIC SUPPRESSOR ELEMENTS

(75) Inventors: Tanya A. Holzmayer; Stephen J. Dunn; Suk W. Park; Andrew Dayn, all of Mountain View, CA (US)

(73) Assignee: Subsidiary No. 3, Inc., Wilmington, NC (US)

( * ) Notice: Subject to any disclaimer, the term of this patent is extended or adjusted under 35 U.S.C. 154(b) by 0 days.

(21) Appl. No.: 08/775,703

(22) Filed: Dec. 18, 1996

Related U.S. Application Data

(63) Continuation-in-part of application No. 08/575,416, filed on Dec. 20, 1995, now abandoned.

(51) Int. Cl.$^7$ ............................................... C07H 21/04
(52) U.S. Cl. ..................... 536/23.72; 435/5; 424/188.1; 424/208.1
(58) Field of Search ............................... 536/23.1, 24.1, 536/23.72; 435/476

(56) References Cited

U.S. PATENT DOCUMENTS 5,695,926 A * 12/1997 Cros et al. ..................... 435/5

FOREIGN PATENT DOCUMENTS

| EP | 594881 | 5/1994 |
|---|---|---|
| WO | WO 90/12087 | 10/1980 |
| WO | WO 90/07936 | 7/1990 |
| WO | WO 92/07071 | 4/1992 |
| WO | WO/ 94/10302 | 5/1994 |
| WO | WO 94/16060 | 7/1994 |
| WO | WO 94/26877 | 11/1994 |
| WO | WO 95/13379 | 5/1995 |

OTHER PUBLICATIONS

Wahl, G.M., et al., 1987, "Molecular Hybridication of Immobilized Nucleic Acids: Theoretical Concepts and Practical Considerations", Meth. Enzymol. 152:399–407.*
Roizman, B., 1990, "Multiplication of Viruses", in *Virology*, Second Edition, Fields et al., eds., Raven Press, Ltd., New York, pp. 88–89.*
Lewin, B., ed., 1987, *Genes*, Third Edition, John Wiley & Sons, New York, pp. 104–105.*

(List continued on next page.)

Primary Examiner—James Housel
Assistant Examiner—Jeffrey S. Parkin
(74) Attorney, Agent, or Firm—McDonnell Boehnen Hulbert & Berghoff

(57) ABSTRACT

The development of general approaches for the isolation of efficient antivirals is becoming increasingly important. The genetic suppressor element (GSE) technology is an approach based on the functional expression and selection of efficient genetic inhibitors from random fragment libraries derived from a gene or genome of interest. We have applied this technology to isolate potent genetic inhibitors against the human immunodeficiency virus type 1 (HIV-1) The strategy employed involved the following steps: 1) fragmenting the HIV-1 genome into 100–700 base pair (bp) fragments; 2) inserting the fragments into expression vectors to form an expression library; 3) transferring the expression library into a population of cells (e.g., OM10.1) containing an inducible latent HIV-1 provirus; 4) selecting a subpopulation of cells which contain a subset of the expression library enriched for HIV-1 GSE by monitoring the expression of a cellular (e.g., CD4) or viral (e.g., p24) marker associated with HIV infection; 5) recovering the GSE from the selected cell population. The GSEs identified clustered in seven narrowly defined regions of the HIV-1 genome and were found to be functionally active. These elements are potential candidates for the gene therapy of AIDS. The developed approaches can be applied to other viral pathogens, as well as, for the identification of cellular genes supporting the HIV-1 life cycle.

8 Claims, 12 Drawing Sheets

OTHER PUBLICATIONS

Figure 1:
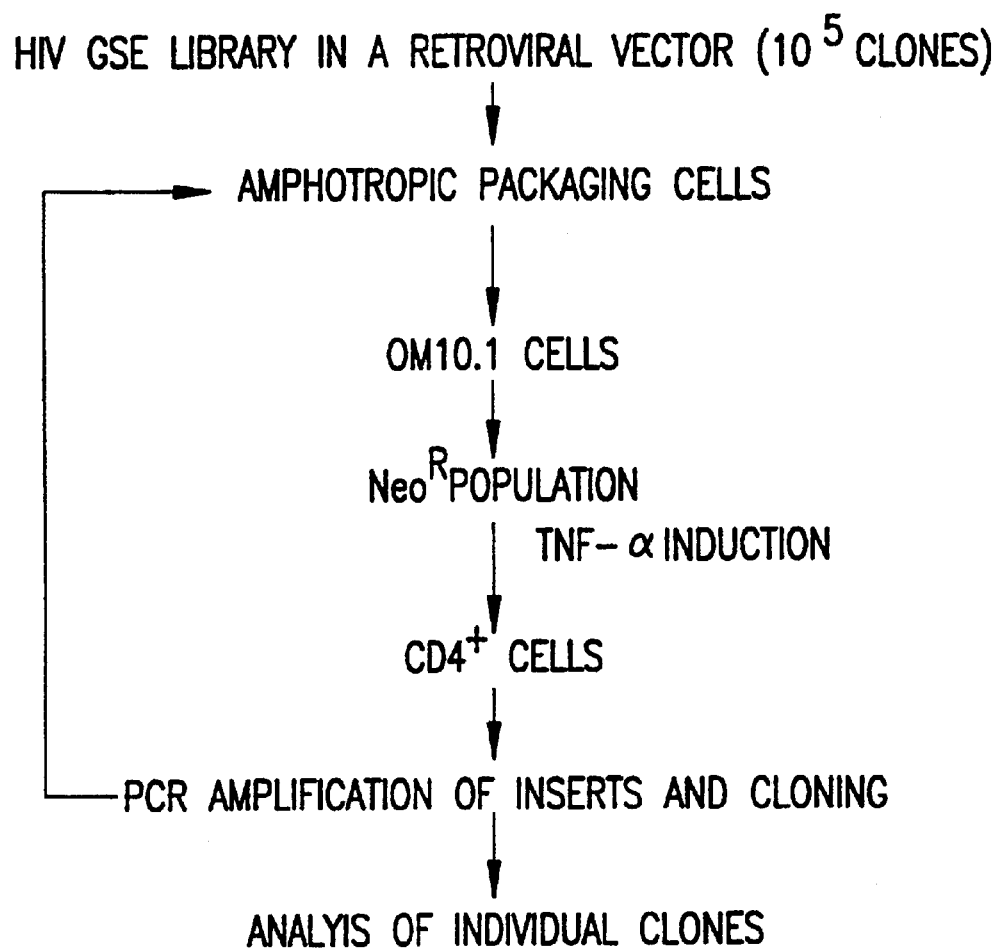

Chatterjee, S., et al., 1992, "Dual–target inhibition of HIV–1 in vitro by means of an adeno–associated virus antisense vector", Science 258:1485–1488.*

Meyer, J., et al., 1993, "Inhibition of HIV–1 replication by a high–copy–number vector expressing antisense RNA for reverse transcriptase", Gene 129:263–268.*

Lo, K.M.S., et al., 1992, "Inhibition of replication of HIV–1 by retroviral vectors expressing tat–antisense and anti–tat ribozyme RNA", Virol. 190:176–183.*

Trono, D., et al., 1989, "HIV–1 Gag mutants can dominantly interfere with the replication of the wild–type virus", Cell 59:113–120.*

Tsunetsugu–Yokota, Y., et al., 1992, "Constitutive expression of the nef gene suppresses human immunodeficiency virus type 1 (HIV–1) replication in monocyte cell lines", Virol. 191:960–963.*

Barre–Sinoussi et al., 1983, Science 220:868–870.
Gallo et al., 1984, Science 224:500–503.
Teich et al., 1984 RNA Tumor Viruses, Weiss et al., eds., CSH–Press, pp. 949–956.
Varmus, 1988, Science 240:1427–1439.
Clavel et al., 1986, Science 233:343–346.
Guyader et al., 1987, Nature 326:662–669.
Dalgleish et al., 1984, Nature 312:763–767.
Klatzman et al., 1984, Nature 312:767–768.
Maddon et al., 1986, Cell 47:333–348.
Smith et al., 1986, Science 232:382–385.
Mitsuya et al., 1991, FASEB J. 5:2369–2381.
Mitsuya et al., 1990, Science 249:1533–1544.
Larder et al., 1989, Science 243:1731–1734.
Smith et al., 1987, Science 238:1704–1707.
Daar et al., 1990, Proc. Natl. Acad. Sci. USA 87:6574–6579.
Schooley et al., 1990, Ann. Int. Med. 112:247–253.
Kahn et al., 1990, Ann. Int. Med. 112–254–261.
Yarchoan et al., 1989, Proc. Vth Int. Conf. on AIDS, p. 564, MCP 137.
Erickson, 1990, Science 249:527–533.
Ventakash et al., 1990, Proc. Natl. Acad. Sci. USA 87:8746–8750.
Brady et al., 1994, Proc. Natl. Acad. Sci. USA 91:365–369.
Malim et al., 1992, J. Exp. Med. 176:1197.
Bevec et al., 1992, Proc. Natl. Acad. Sci. USA 89:9870–74.
Woffendin et al., 1994, Proc. Natl. Acad. Sci. USA 91:11581–85.
Lee et al., 1994, J. Virology 68:8254–64.
Marasco et al., 1993, Proc. Natl. Acad. Sci. USA 90:7889–93.
Chatterjee et al., 1992, Science 258:1485.
Ojwang et al., 1992 Proc. Natl. Acad. Sci. USA 89:10802–06.
Yamada et al., 1994, Gene Therapy 1:38–45.
Miller and Rosman, 1989, BioTechniques 7:980.
Miller and Buttimore, 1986, Mol. Cell. Biol. 6:2895–2902;ATCC CRL #9078.
Bednarkik and Folks, 1992, AIDS 6:3–16.
Poli and Fauci, 1992, AIDS Res. Human Retroviruses 9:191–197.
Foley et al., 1965, Cancer 18:522–29.
Nara & Fischinger, 1988, Nature 322:469–70.
Bittner et al., 1987, Methods in Enzymol. 153:516–544.
Logan & Shenk, 1984, Proc. Natl. Acad. Sci. USA 81:3655–3659.

* cited by examiner

ACATTTAGAA GGAAAAGTTA TCCTGGTAGC AGTTCATGTA GCCAGTGGAT
ATATAGAAGC AGAAGTTATT CCAGCAGAAA CAGGGCAGGA AACAGCATAC
TTTCTTTTAA AATTAGCAGG AAGATGGCCA GTAAAAACAA TACATACAGA
CAATGGCAGC AATTTCACCA GT

FIG.4

ACAAATAGGA TGGATGACAA ATAATCCACC TATCCCAGTA GGAGAAATTT
ATAAAGATG GATAATCCTG GGATTAAATA AAATAGTAAG AATGTATAGC
CCTACCAGCA TTCTGGACAT AAGACAAGGA CCAAAAGAAC CCTTTAGAGA
CTATGTAGAC CGGTTCTATA AAACTCTAAG AGCCGAGCAA GCTTCACAGG
AGGTAAAAAA TTGGATGACA GAAACCTTGT TGGTCCAAAA TGCGA

FIG.5

GATGACAAAT AATCCACCTA TCCCAGTAGG AGAAATTTAT AAAAGATGGA
TAATCCTGGG ATTAAATAAA ATAGTAAGAA TGTATAGCCC TACCAGCATT
CTGGACATAA GACAAGGACC AAAAGAACCC TTTAGAGACT ATGTAGACCG
GTTCTATAAA ACTCTAAGAG CCGAGCAAGC TTCACAGGAG GTAAAAAATT
GGATGACAGA AACCTTGTTG GTCCAAAATG C

FIG.6

GTGGGAGCAG TATCTCGAGA CCTGGAAAAA CATGGAGCAA TCACAAGTAG
CAATACAGCA GCTACTAATG CTGATTGTGC CTGGCTAGAA GCA

FIG.7

CCTCAGACCC TTTTAGTCAG TGTGGAAAAT CTCTAGCAGT GGCGCCCGAA
CAGGGACTTG AAAGCGAAAG GGAAACCAGA GGAGCTCTCT CGACGCAGGA
CTCGGCTTGC

FIG.8

```
GACGGCTGGG CCCGACGGAA TCGAAGAAGA AGGTGGAGAG AGAGACAGAG
ACAGATCCGT TCGATTAGTG TATGGATTCT TAGCACTTAT CTGGGAAGAT
CTGCGGAGCC TGTGCCTCTT CAGCTACCGC CGCT
```

FIG.9

```
TCAAATATTG GTGGAATCTC CTACAGTATT GGAGTCAGGA ACTAAAGAAT
AGTGCTGTTA GCTTGCTCAA TGCCACAGCC ATAGCAGTAG CTGAGGGGAC
AGATAGGGTT ATAGAAGTAG TACAAGGAGC TTGTAAGCTA TTCGCCACAT
ACCTAGAAGA ATAAGACAGG GCTTGGAAAG GATTTTGCTA TAAGATGGGT
GGCAAGTGGT CAAAAAGTAG TGTGGTTGGA TGGCCTACTG TAAGGGAAAG
AATGAGACGA GCTGAGCCAG CAGCAGATGG GGTGGGAGCA GCATCTCGAG
ACCTGGAAAA ACATGGAGCA ATCACAAGTA GCAATACA
```

FIG.10

```
AGCACACAAA GGAATTGGAG GAAATGAACA AGTAGATAAA TTAGTCAGTG
CTGGAATCAG GAAAGTACTA TTTTTAGATG GAATAGATAA GGCCCAAGAT
GAACATGAGA AATATCACAG TAATTGGAGA GCAATGGCTA GTGATTTTAA
CCTGCCACCT GTAGTAGCAA AAGAAATAGT AGCCAGC
```

FIG.11

```
                              SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:1:

CTCGGAATTC AAGCTTATGG ATGGATG                                             27

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:2:

CATCCATCCA TAAGCTTGAA TTCC                                                24

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear
```

(xi) SEQUENCE DESCRIPTION: SEQ ID NO:3:

TGAGTGAGTG AATCGATGGA TCCGTCT                                              27

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:4:

TCCTAGACGG ATCCATCGAT TCACTCACTC A                                         31

(2) INFORMATION FOR SEQ ID NO:5:

(i) SEQUENCE CHARACTERISTICS:
        (A) LENGTH: 172 base pairs
        (B) TYPE: nucleic acid
        (C) STRANDEDNESS: single
        (D) TOPOLOGY: linear (xi) SEQUENCE DESCRIPTION: SEQ ID NO:5:

ACATTTAGAA GGAAAAGTTA TCCTGGTAGC AGTTCATGTA GCCAGTGGAT ATATAGAAGC           60

AGAAGTTATT CCAGCAGAAA CAGGGCAGGA AACAGCATAC TTTCTTTTAA AATTAGCAGG          120

AAGATGGCCA GTAAAAACAA TACATACAGA CAATGGCAGC AATTTCACCA GT                  172

(2) INFORMATION FOR SEQ ID NO:6:

(i) SEQUENCE CHARACTERISTICS:
        (A) LENGTH: 245 base pairs
        (B) TYPE: nucleic acid
        (C) STRANDEDNESS: single
        (D) TOPOLOGY: linear (xi) SEQUENCE DESCRIPTION: SEQ ID NO:6:

ACAAATAGGA TGGATGACAA ATAATCCACC TATCCCAGTA GGAGAAATTT ATAAAAGATG           60

GATAATCCTG GGATTAAATA AAATAGTAAG AATGTATAGC CCTACCAGCA TTCTGGACAT         120

AAGACAAGGA CCAAAAGAAC CCTTTAGAGA CTATGTAGAC CGGTTCTATA AAACTCTAAG         180

AGCCGAGCAA GCTTCACAGG AGGTAAAAAA TTGGATGACA GAAACCTTGT TGGTCCAAAA         240

TGCGA                                                                    245

(2) INFORMATION FOR SEQ ID NO:7:

(i) SEQUENCE CHARACTERISTICS:
        (A) LENGTH: 231 base pairs
        (B) TYPE: nucleic acid
        (C) STRANDEDNESS: single
        (D) TOPOLOGY: linear (xi) SEQUENCE DESCRIPTION: SEQ ID NO:7:

GATGACAAAT AATCCACCTA TCCCAGTAGG AGAAATTTAT AAAAGATGGA TAATCCTGGG           60

ATTAAATAAA ATAGTAAGAA TGTATAGCCC TACCAGCATT CTGGACATAA GACAAGGACC         120

AAAAGAACCC TTTAGAGACT ATGTAGACCG GTTCTATAAA ACTCTAAGAG CCGAGCAAGC         180

TTCACAGGAG GTAAAAAATT GGATGACAGA AACCTTGTTG GTCCAAAATG C                  231

(2) INFORMATION FOR SEQ ID NO:8:

(i) SEQUENCE CHARACTERISTICS:
        (A) LENGTH: 93 base pairs (B) TYPE: nucleic acid
(C) STRANDEDNESS: single
(D) TOPOLOGY: linear (xi) SEQUENCE DESCRIPTION: SEQ ID NO:8:

| | | | | | |
|---|---|---|---|---|---|
| GTGGGAGCAG | TATCTCGAGA | CCTGGAAAAA | CATGGAGCAA | TCACAAGTAG | CAATACAGCA | 60 |
| GCTACTAATG | CTGATTGTGC | CTGGCTAGAA | GCA | | | 93 |

(2) INFORMATION FOR SEQ ID NO:9:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (xi) SEQUENCE DESCRIPTION: SEQ ID NO:9:

| | | | | | |
|---|---|---|---|---|---|
| CCTCAGACCC | TTTTAGTCAG | TGTGGAAAAT | CTCTAGCAGT | GGCGCCCGAA | CAGGGACTTG | 60 |
| AAAGCGAAAG | GGAAACCAGA | GGAGCTCTCT | CGACGCAGGA | CTCGGCTTGC | | 110 |

(2) INFORMATION FOR SEQ ID NO:10:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO:10:

| | | | | | |
|---|---|---|---|---|---|
| GACGGCTGGG | CCCGACGGAA | TCGAAGAAGA | AGGTGGAGAG | AGAGACAGAG | ACAGATCCGT | 60 |
| TCGATTAGTG | TATGGATTCT | TAGCACTTAT | CTGGGAAGAT | CTGCGGAGCC | TGTGCCTCTT | 120 |
| CAGCTACCGC | CGCT | | | | | 134 |

(2) INFORMATION FOR SEQ ID NO:11:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (xi) SEQUENCE DESCRIPTION: SEQ ID NO:11:

| | | | | | |
|---|---|---|---|---|---|
| TCAAATATTG | GTGGAATCTC | CTACAGTATT | GGAGTCAGGA | ACTAAAGAAT | AGTGCTGTTA | 60 |
| GCTTGCTCAA | TGCCACAGCC | ATAGCAGTAG | CTGAGGGGAC | AGATAGGGTT | ATAGAAGTAG | 120 |
| TACAAGGAGC | TTGTAAGCTA | TTCGCCACAT | ACCTAGAAGA | ATAAGACAGG | GCTTGGAAAG | 180 |
| GATTTTGCTA | TAAGATGGGT | GGCAAGTGGT | CAAAAAGTAG | TGTGGTTGGA | TGGCCTACTG | 240 |
| TAAGGGAAAG | AATGAGACGA | GCTGAGCCAG | CAGCAGATGG | GGTGGGAGCA | GCATCTCGAG | 300 |
| ACCTGGAAAA | ACATGGAGCA | ATCACAAGTA | GCAATACA | | | 338 |

(2) INFORMATION FOR SEQ ID NO:12:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (xi) SEQUENCE DESCRIPTION: SEQ ID NO:12:

| | | | | | |
|---|---|---|---|---|---|
| AGCACACAAA | GGAATTGGAG | GAAATGAACA | AGTAGATAAA | TTAGTCAGTG | CTGGAATCAG | 60 |
| GAAAGTACTA | TTTTTAGATG | GAATAGATAA | GGCCCAAGAT | GAACATGAGA | AATATCACAG | 120 |

```
TAATTGGAGA GCAATGGCTA GTGATTTTAA CCTGCCACCT GTAGTAGCAA AAGAAATAGT    180

AGCCAGC                                                              187
```

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ix) FEATURE:
        (A) NAME/KEY: Coding S equence
        (B) LOCATION: 22...42
        (D) OTHER INFORMATION:

(xi) SEQUENCE DESCRIPTION: SEQ ID NO:13:

```
GAATTCAAGC TTGCCGCCAC C ATG GGC CCG ACG GAA TCG AAG           42
                       Met Gly Pro Thr Glu Ser L ys
                        1                   5
```

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:14:

```
Met Gly Pro Thr Glu Ser Lys
 1                   5
```

(2) INFORMATION FOR SEQ ID NO:15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ix) FEATURE:
        (A) NAME/KEY: Coding S equence
        (B) LOCATION: 22...45
        (D) OTHER INFORMATION:

(xi) SEQUENCE DESCRIPTION: SEQ ID NO:15:

```
GAATTCAAGC TTGCCGCCAC C ATG GAC GGG CCC GAC GGA ATC GAA       45
                       Met Asp Gly Pro Asp Gly I le Glu
                        1                   5
```

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:16:

Met Asp Gly Pro Asp Gly Ile Glu

-continued

```
 1               5

(2) INFORMATION FOR SEQ ID NO:17:

(i) SEQUENCE CHARACTERISTICS:
          (A) LENGTH: 48 base pairs
          (B) TYPE: nucleic acid
          (C) STRANDEDNESS: single
          (D) TOPOLOGY: linear (ix) FEATURE:
          (A) NAME/KEY: Coding S equence
          (B) LOCATION: 22...48
          (D) OTHER INFORMATION:

(xi) SEQUENCE DESCRIPTION: SEQ ID NO:17:

GAATTCAAGC TTGCCGCCAC C ATG GAC GGC TGG GCC CGA CGG AAT CGA          48
                        Met Asp Gly Trp Ala Arg A rg Asn Arg
                         1               5

(2) INFORMATION FOR SEQ ID NO:18:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: protein (v) FRAGMENT TYPE: internal (xi) SEQUENCE DESCRIPTION: SEQ ID NO:18:

Met Asp Gly Trp Ala Arg Arg Asn Arg
 1               5
```

NUCLEIC ACIDS ENCODING HUMAN IMMUNODEFICIENCY VIRUS TYPE 1 GENETIC SUPPRESSOR ELEMENTS

This application is a continuation-in-part application of U.S. Ser. No. 08/575,416, filed Dec. 20, 1995, now abandoned.

1. INTRODUCTION

The present invention relates to genetic elements that suppress the activities of the human immunodeficiency virus (HIV). In particular, the invention relates to polynucleotides isolated from the HIV-1 genome, methods for isolating and identifying such polynucleotides, and methods for using them for the protection of human cells against HIV infection and/or replication.

2. BACKGROUND OF THE INVENTION

2.1. The Human Immunodeficiency Virus

The primary cause of acquired immunodeficiency syndrome (AIDS) has been shown to be HIV (Barre-Sinoussi et al., 1983, Science 220:868–870; Gallo et al., 1984, Science 224:500–503). HIV causes immunodeficiency in an individual by infecting important cell types of the immune system, which results in their depletion. This, in turn, leads to opportunistic infections, neurological dysfunctions, neoplastic growth, and death.

HIV is a member of the lentivirus family of retroviruses (Teich et al., 1984, RNA Tumor Viruses, Weiss et al., eds., CSH-Press, pp. 949–956). Retroviruses are small enveloped viruses that contain a diploid, single-stranded RNA genome, and replicate via a DNA intermediate produced by a virally-encoded reverse transcriptase, an RNA-dependent DNA polymerase (Varmus, 1988, Science 240:1427–1439). There are at least two distinct subtypes of HIV: HIV-1 (Barre-Sinoussi et al., 1983, Science 220:868–870; Gallo et al., 1984, Science 224:500–503) and HIV-2 (Clavel et al., 1986, Science 233:343–346; Guyader et al., 1987, Nature 326:662–669). Genetic heterogeneity exists within each of these HIV subtypes.

CD4$^+$ T cells are the major targets of HIV infection because the CD4 cell surface protein acts as a cellular receptor for HIV attachment (Daigleish et al., 1984, Nature 312:763–767; Klatzmann et al., 1984, Nature 312:767–768; Maddon et al., 1986, Cell 47:333–348). Viral entry into cells is dependent upon viral protein gp120 binding to the cellular CD4 receptor molecule (McDougal et al., 1986, Science 231:382–385; Maddon et al., 1986, Cell 47:333–348).

2.2. HIV Treatment

HIV infection is pandemic and HIV-associated diseases have become a world-wide health problem. Despite considerable efforts in the design of anti-HIV modalities, there is, thus far, no successful prophylactic or therapeutic regimen against AIDS. However, several stages of the HIV life cycle have been considered as potential targets for therapeutic intervention (Mitsuya et al., 1991, FASEB J. 5:2369–2381). For example, virally-encoded reverse transcriptase has been a major focus of drug development. A number of reverse-transcriptase-targeted drugs, including 2',3'-dideoxynucleotide analogs such as AZT, ddI, ddC, and ddT have been shown to be active against HIV (Mitsuya et al., 1990, Science 249:1533–1544). While beneficial, these nucleotide analogs are not curative, probably due to the rapid appearance of drug resistant HIV mutants (Lander et al., 1989, Science 243:1731–1734). In addition, the drugs often exhibit toxic side effects, such as bone marrow suppression, vomiting, and liver abnormalities.

Another stage of the HIV life cycle that has been targeted is viral entry into the cells, the earliest stage of HIV infection. This approach has primarily utilized recombinant soluble CD4 protein to inhibit infection of CD4$^+$ T cells by some HIV-1 strains (Smith et al., 1987, Science 238:1704–1707). Certain primary HIV-1 isolates, however, are relatively less sensitive to inhibition by recombinant CD4 (Daar et al., 1990, Proc. Natl. Acad. Sci. USA 87:6574–6579). To date, recombinant soluble CD4 clinical trials have produced inconclusive results (Schooley et al., 1990, Ann. Int. Med. 112:247–253; Kahn et al., 1990, Ann. Int. Med. 112:254–261; Yarchoan et al., 1989, Proc. Vth Int. Conf. on AIDS, p. 564, MCP 137).

The later stages of HIV replication, which involve crucial virus-specific secondary processing of certain viral proteins, have also been examined as possible anti-HIV drug targets. Late stage processing is dependent on the activity of a viral protease, and drugs have been developed to inhibit this protease (Erickson, 1990, Science 249:527–533). However, the clinical utility of these candidate drugs is still in question.

The lack of a satisfactory treatment for AIDS has led investigators to gene therapy approaches. One form of gene therapy involves the use of genetically-engineered viral vectors to introduce toxic gene products to kill HIV-infected cells. For instance, replication defective vectors have been designed to introduce cell growth inhibitory genes into host cells (WO 90/12087, Oct. 18, 1980). One strategy attempted by several groups involves the delivery of the herpes simplex virus type 1 thymidine kinase (tk) toxin gene. The tk gene product is toxic to mammalian cells only in the presence of nucleoside analogs, such as ganciclovir (Ventakash et al., 1990, Proc. Natl. Acad. Sci. USA 87: 8746–8750; Brady et al., 1994, Proc. Natl. Acad. Sci. USA 91: 365–369; WO 90/07936, Jul. 26, 1990). Diphtheria toxin gene has also been used, and the gene was placed under the control of cis-acting HIV regulatory sequences (U.S. Pat. No. 5,306,631, issued Apr. 26, 1994). Others have utilized replication incompetent mutants of HIV which have the potential to express an inhibitory gene product in the presence of HIV tat (WO 94/16060, Jul. 21, 1994).

Another form of gene therapy is designed to protect virally-infected cells from cytolysis by specifically disrupting viral replication. Efforts to identify appropriate protective genes have, in large part, been based on an understanding of the molecular biology of HIV replication. A few examples of this approach are as follows.

The HIV-1 Rev gene encodes a protein that is necessary for the expression of full length HIV-1 transcripts in infected cells and the production of HIV-1 virions. Transfection with one Rev mutant known as RevM10 has been shown to protect the cells against HIV infection (Malim et al., 1992, J. Exp. Med. 176:1197; Bevec et al., 1992, Proc. Natl. Acad. Sci. USA 89:9870–74). Typically, the transfectants are resistant to HIV-1 infection for about 2 weeks from the time of inoculation before resistant variants appear (Woffendin et al., 1994, Proc. Natl. Acad. Sci. USA 91: 11581–85).

In addition, Rev function can be interfered with by producing an excess of the binding site of the Rev protein, termed Rev Response Element (RRE), which prevents the binding of Rev to RRE of viral transcripts. A "decoy" which consisted of a chimeric RNA composed of an RRE and a tRNA prevented infection of cultured cells for a period of greater than about 40 days (Lee et al., 1994, J.Virology 68:8254–64).

Alternatively, fusion proteins capable of binding to viral env proteins have been made to prevent the production of HIV-1 virions. Examples include a fusion protein composed of CD4 and a lysosomal targeting protein procathepsin D, and an anti-env Fv which is secreted into the endoplasmic reticulum (Lin et al., WO 93/06216; Marasco et al., 1993, Proc. Natl. Acad. Sci. USA 90:7889–93).

Antisense polynucleotides have also been designed to complex with and sequester the HIV-1 transcripts (Holmes et al., WO 93/11230; Lipps et al., WO 94/10302; Kretschmer et al., EP 594,881; and Chatterjee et al., 1992, Science 258:1485). Furthermore, an enzymatically active RNA, termed ribozyme, has been used to cleave viral transcripts. The ribozyme approach to forming an HIV-1 resistant hematopoietic cell line has been reported (Ojwang et al., 1992, Proc. Natl. Acad. Sci. USA 89:10802–06; Yamada et al., 1994, Gene Therapy 1:38–45; Ho et al., WO 94/26877; and Cech and Sullenger, WO 95/13379).

Roninson et al. described a method for isolating genetic fragments from the HIV-1 genome capable of protecting a cell from HIV-1 infection (U.S. Pat. No. 5,217,889 and WO 92/07071). The method involves the preparation of an expression library known as a Random Fragment Expression (RFE) library that contains random sequence fragments of the HIV-1 genome. Gene fragments referred to as HIV-1 Genetic Suppressor Elements (HIV-1 GSE) are then selected from the RFE library following an extensive selection procedure. The selection step involves transfection of the RFE library into a cell line to which HIV-1 infection is normally cytotoxic. However, the low sensitivity of this selection step greatly limits the practical use of the procedure. Moreover, no specific GSE sequences were reported using this method that were capable of suppressing HIV-1 infection.

3. SUMMARY OF THE INVENTION

The present invention relates to specific HIV-derived polynucleotides herein referred to as GSE that suppress HIV infection and/or replication in human cells, methods for isolating and identifying such polynucleotides, and methods for using them in the prevention and treatment of HIV infection.

The invention is based, in part, on the Applicants' discovery that nucleotide fragments can be isolated from the HIV-1 genome, based on their ability to suppress the activation of latent HIV-1 in a CD4+ cell line. In this connection, any cellular or viral marker associated with HIV replication can be used to monitor the activation of latent HIV. An example of such a marker is CD4, which is conveniently monitored by using a specific antibody. While the majority of the cells lose cell surface CD4 expression after induction of the virus from latency, the cells containing HIV-1 GSE retain CD4 expression. A number of novel HIV-1 GSE polynucleotides are selected on the basis of their ability to sustain CD4 expression by the induced cells, and several of such sequences are further shown to protect uninfected T cells from productive infection by HIV-1. The GSE may function in the form of an RNA product or protein product, both of which are within the scope of the invention.

A wide range of uses are encompassed by the invention, including but not limited to, AIDS treatment and prevention by transferring GSE into HIV-1-susceptible cell types. For example, GSE may be transferred into hematopoietic stem cells in vitro followed by their engraftment in an autologous, histocompatible or even histoincompatibile recipient. In an alternative embodiment of the invention, any cells susceptible to HIV infection may be directly transduced or transfected with GSE in vivo.

4. BRIEF DESCRIPTION OF THE DRAWINGS

FIG. 1. Schematic representation of the process of using OM10.1 cells to select active HIV-1 GSE clones from an HIV-1 RFE library.

Figure 2:
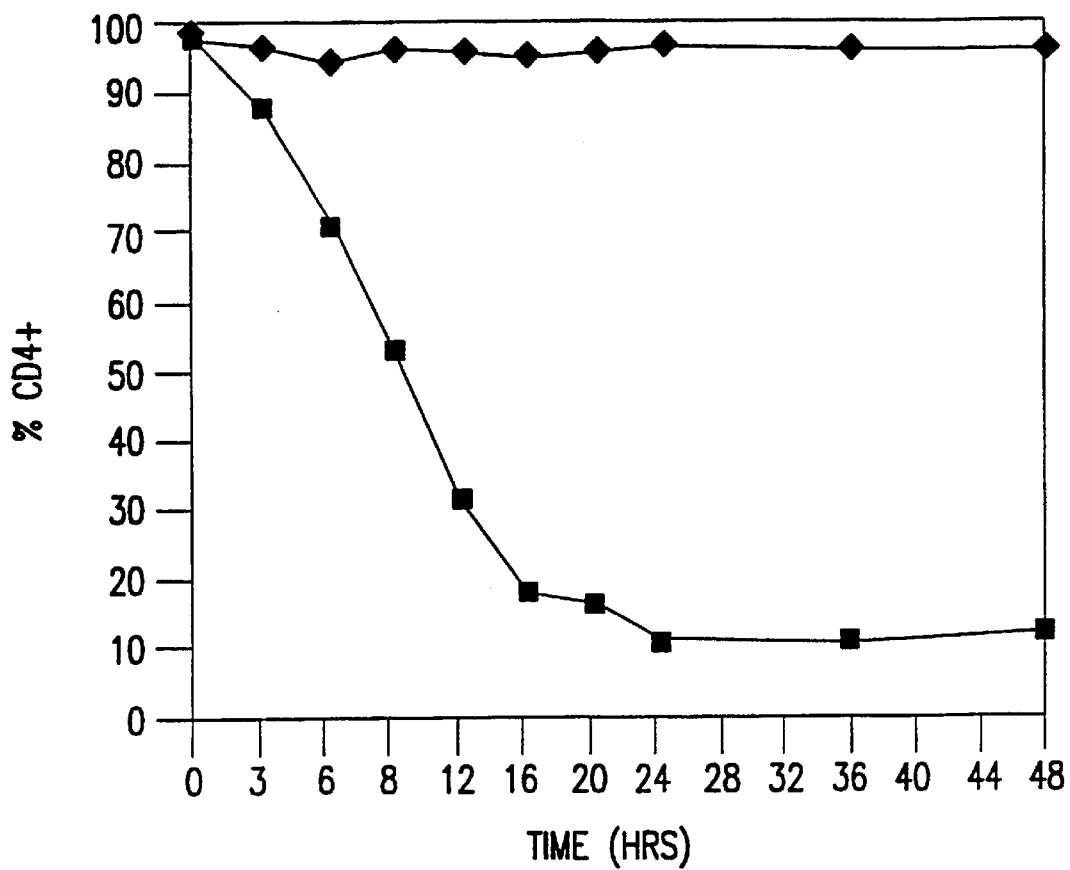

FIG. 2. Percentage of CD4+ OM10.1 cells diminishes after TNF-α induction; TNF-induced cells, -■-; uninduced cells, -♦-.

Figure 3:
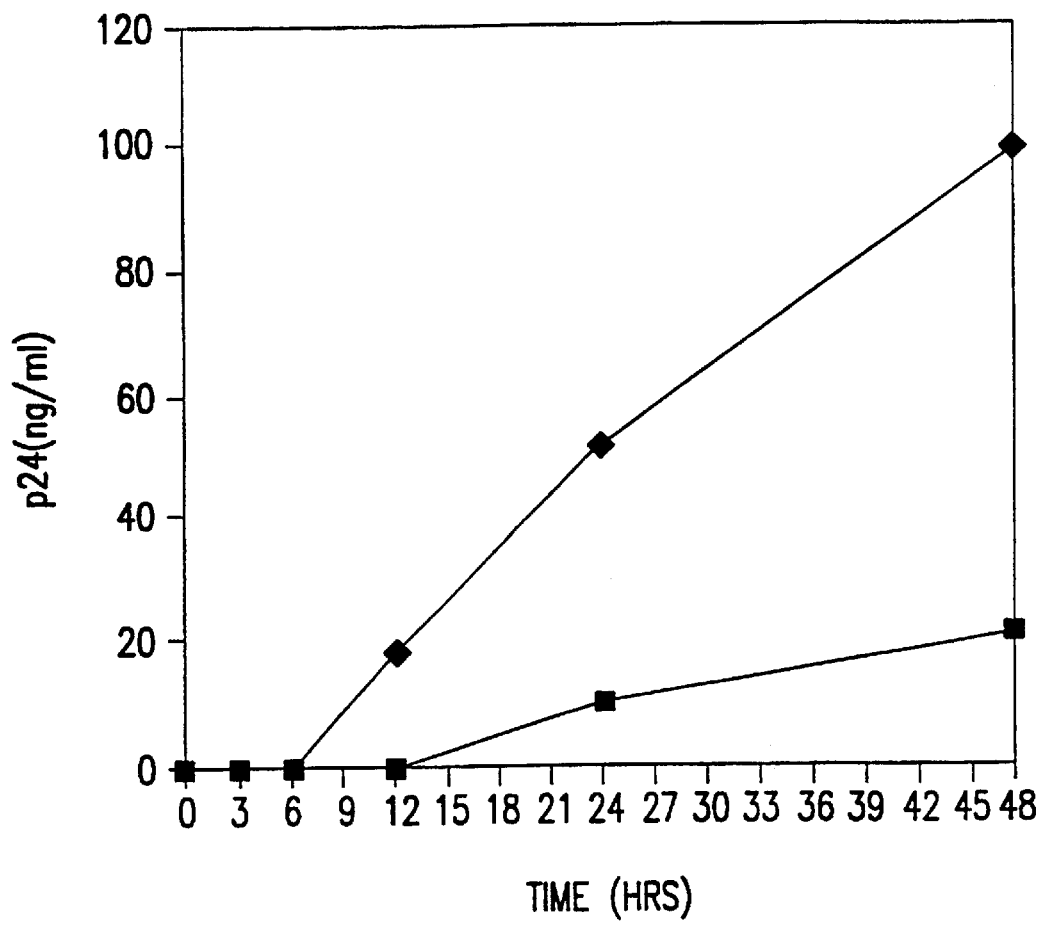

FIG. 3. HIV p24 level increases in OM10.1 cells after TNF-α induction; TNF-induced cells, -♦-;. uninduced cells,-■-.

FIG. 4. GSE IGX-004 nucleotide sequence (SEQ ID NO:5) in the sense orientation is selected for its ability to maintain CD4 expression by OM10.1 cells after TNF-α induction.

FIG. 5. GSE IGX-024 nucleotide sequence (SEQ ID NO:6) in the sense orientation is selected for its ability to maintain CD4 expression by OM10.1 cells after TNF-α induction.

FIG. 6. GSE IGX-042 nucleotide sequence (SEQ ID NO:7) in the sense orientation is selected for its ability to maintain CD4 expression by OM10.1 cells after TNF-α induction.

FIG. 7. GSE IGX-009 nucleotide sequence (SEQ ID NO:8) in the sense orientation is selected for its ability to maintain CD4 expression by OM10.1 cells after TNF-α induction.

FIG. 8. GSE IGX-005 nucleotide sequence (SEQ ID NO:9) in the sense orientation is selected for its ability to maintain CD4 expression by OM10.1 cells after TNF-α induction.

FIG. 9. GSE IGX-230 nucleotide sequence (SEQ ID NO:10) in the sense orientation is selected for its ability to maintain CD4 expression by OM10.1 cells after TNF-α induction.

FIG. 10. GSE IGX-003 nucleotide sequence (SEQ ID NO:11) in the anti-sense orientation is selected for its ability to maintain CD4 expression by OM10.1 cells after TNF-α induction.

FIG. 11. GSE IGX-170 nucleotide sequence (SEQ ID NO:12) in the anti-sense orientation is selected for its ability to maintain CD4 expression by OM10.1 cells after TNF-α induction.

Figure 12:
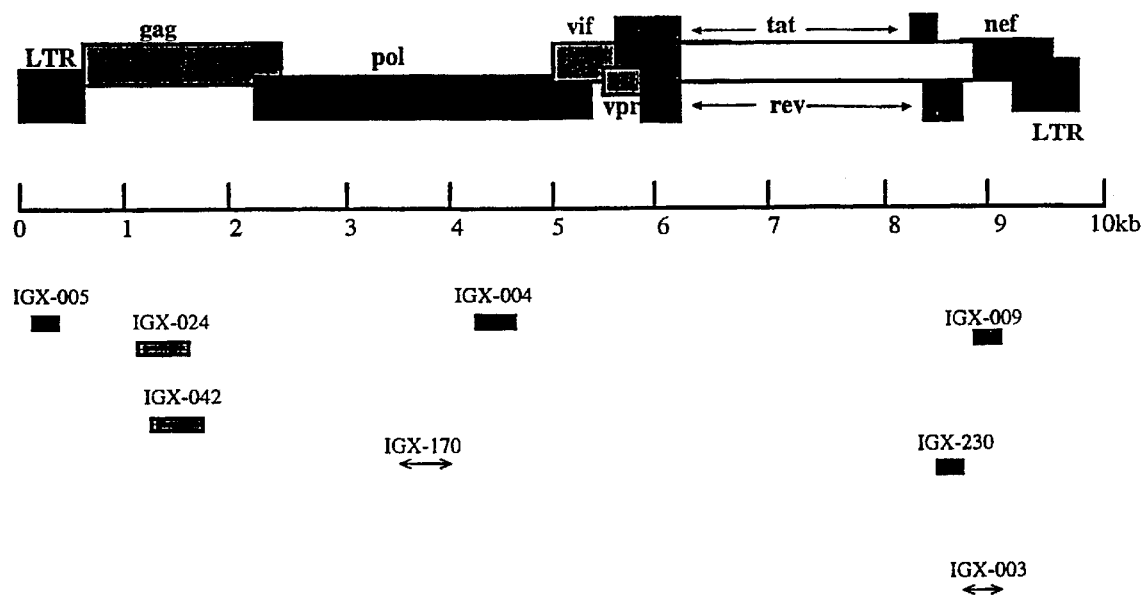

FIG. 12. Location of HIV GSE on the HIV-1 genome. Arrows indicate antisense orientation elements, while boxes indicate sense orientation elements.

Figure 13:
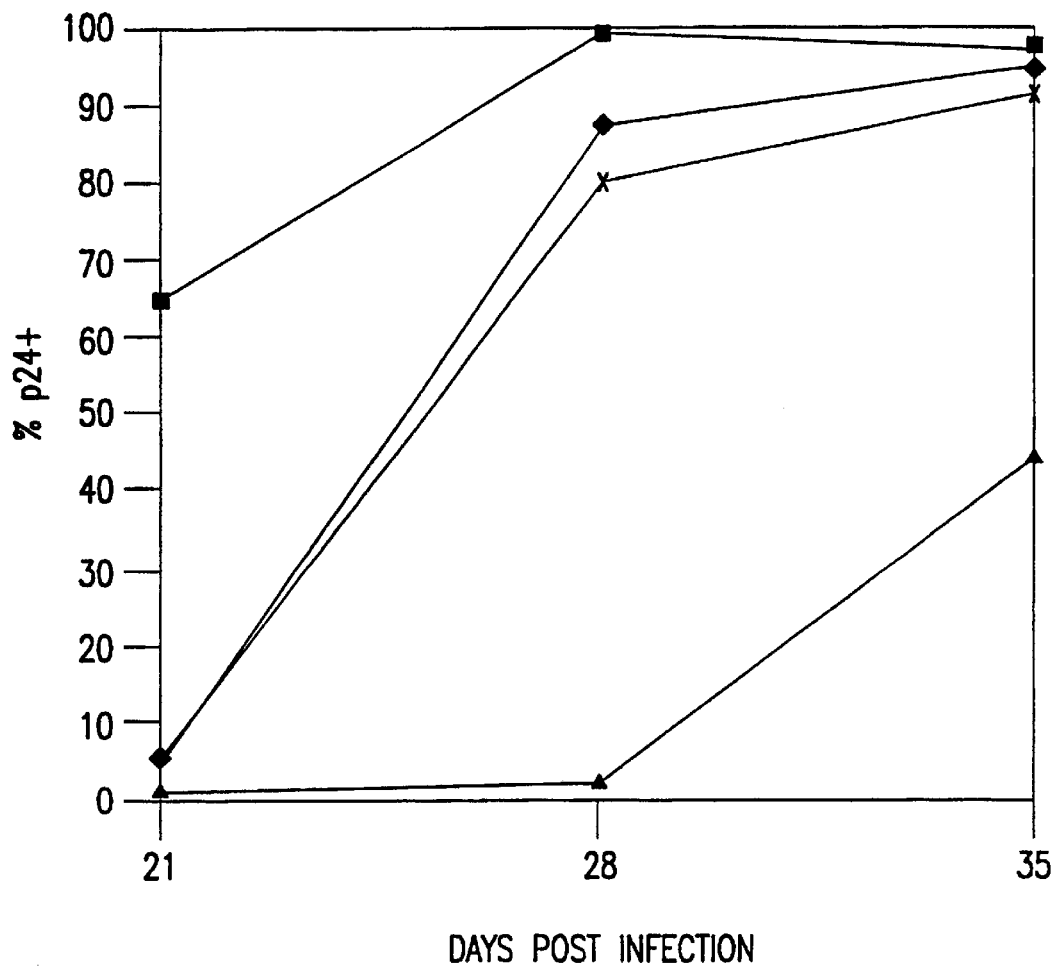

FIG. 13. Percentage of intracellular p24$^{30}$ cells after infection with HIV-1$_{SF2}$ at a TCID$_{50}$ of 200. CEM-ss cells (10$^6$) containing GSE were harvested at 21, 28 and 35 days after infection with HIV, stained with FITC-conjugated anti-p24 antibody and analyzed by flow cytometry. Transduced sequences: REVM10, -♦-; plasmid DNA (negative control), -■-; IGX-004, -▼-; IGX-230, -x-.

Figure 14:
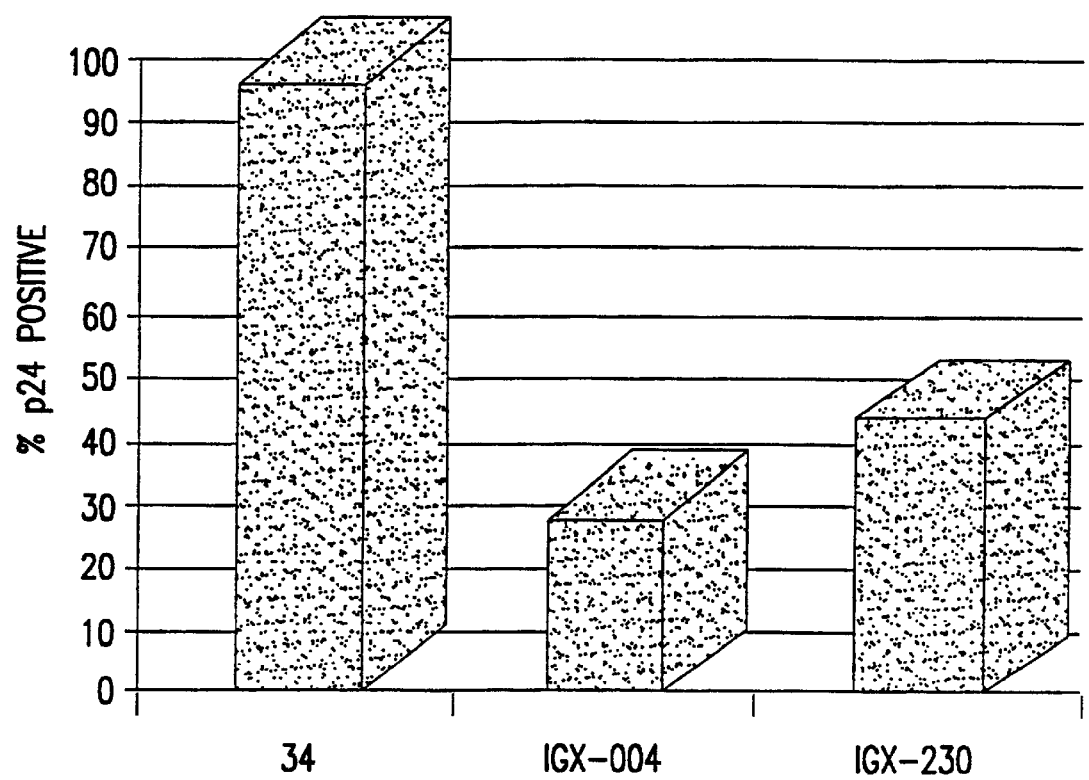

FIG. 14. Percentage of intracellular p24+ cells after infection with HIV-1$_{SF33}$ at a TCID$_{50}$ of 1000. CEM-ss cells (10$^6$) containing GSE were harvested at 9 days after infection with HIV, stained with FITC-conjugated anti-p24 and analyzed by flow cytometry.

Figure 15:
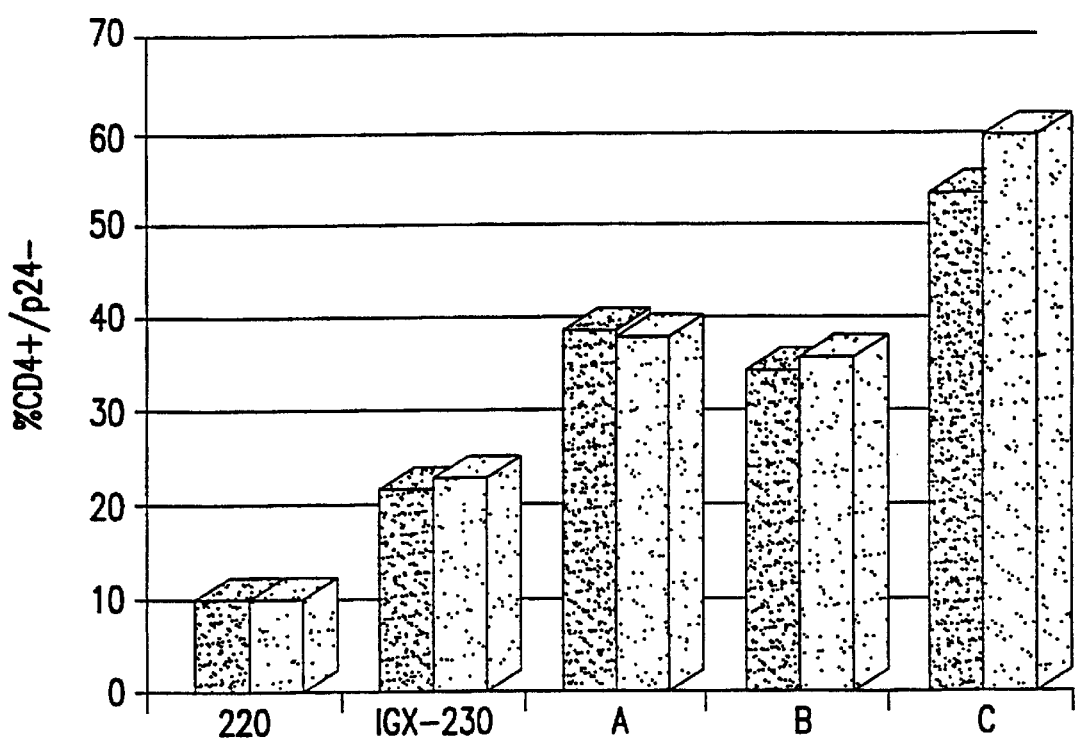

FIG. 15. Percentage of CD4+ and p24$^-$OM10.1 cells containing IGX-230 constructs after TNF-α induction. OM10.1 cells containing 220 (plasmid DNA in LXSN vector), the IGX-230 sequence, or constructs representing the three potential reading frames of the IGX-230 sequence (A, B, C) were induced with TNF-α and analyzed 24 hours later for CD4 expression (dark column) and intracellular p24 (light column representing absence of p24) levels. A corresponds to Tat, B corresponds to envelope, and C corresponds to Rev. Primers used for constructs representing the three potential reading frames (A, B, C) are as follows:

```
A.  5'-G GAA TTC AAG CTT GCC GCC ACC ATG GGC CCG ACG GAA TCG AA(G)      (SEQ ID NO: 13)
        EcoRI   HindIII              Met Gly Pro Thr Glu Ser Lys         (SEQ ID NO: 14)

B.  5'-G GAA TTC AAG CTT GCC GCC ACC ATG GAC GGG CCC GAC GGA ATC GGA    (SEQ ID NO: 15)
        EcoRI   HindIII              Met Asp Gly Pro Asp Gly Ile Glu     (SEQ ID NO: 16)

C.  5'-G GAA TTC AAG CTT GCC GCC ACC ATG GAC GGC TGG GCC CGA CGG AAT CGA (SEQ ID NO: 17)
        EcoRI   HindIII              Met Asp Gly Trp Ala Arg Arg Asn Arg (SEQ ID NO: 18)
```

Figure 16:
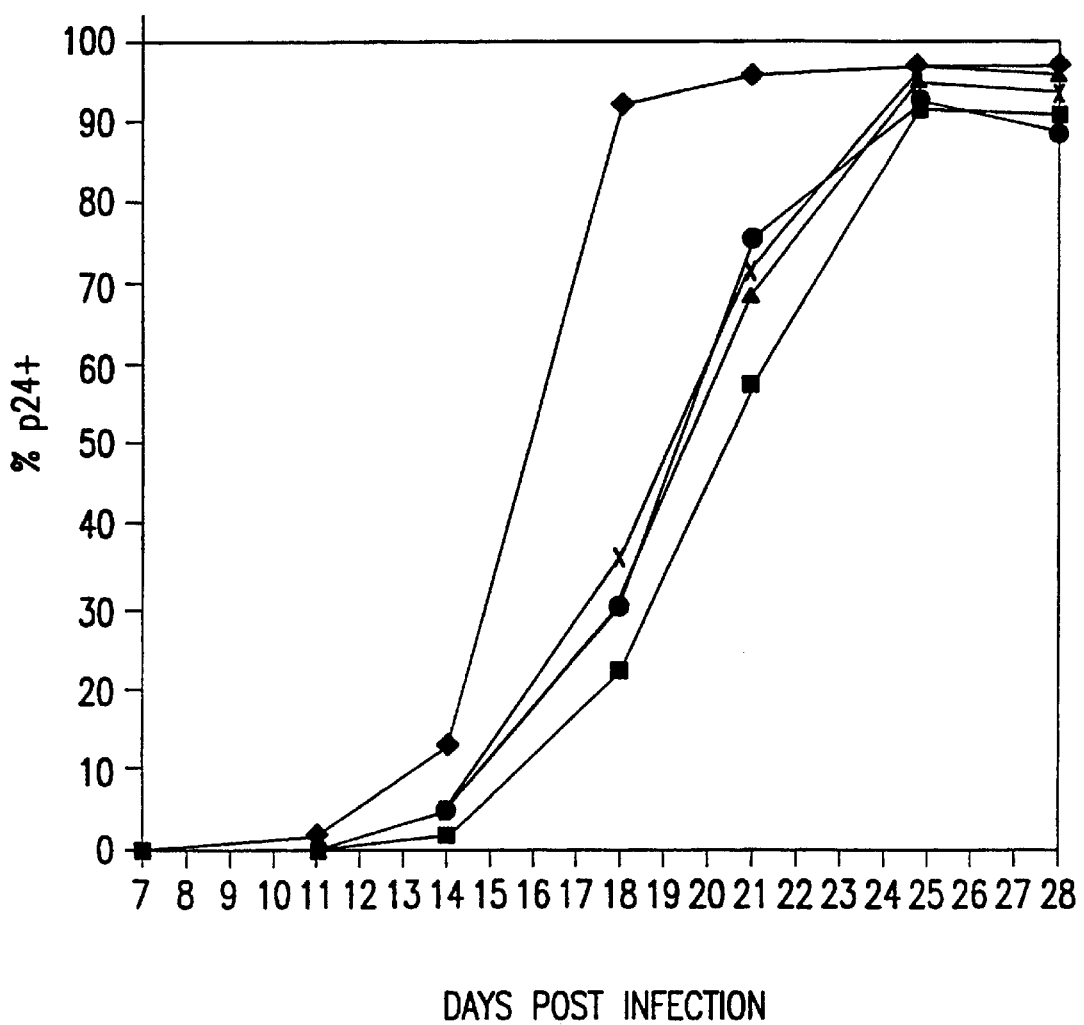

FIG. 16. Percentage of intracellular p24+ CEM-ss cells containing the IGX-230 constructs (the three open reading frames are denoted as A, B, C) after infection with HIV-1$_{SF2}$ at a TCID$_{50}$ of 500. CEM-ss cells ($10^6$) containing the IGX-230 constructs, 34 (plasmid DNA in LXSN), or the RevM10 in LNCX were harvested on the indicated days post infection, stained with FITC-conjugated anti-p24 and analyzed by flow cytometry. Negative control (34), -♦-; REVM10, -■-; A, -▼-; B, -x-; C, -*-.

Figure 17:
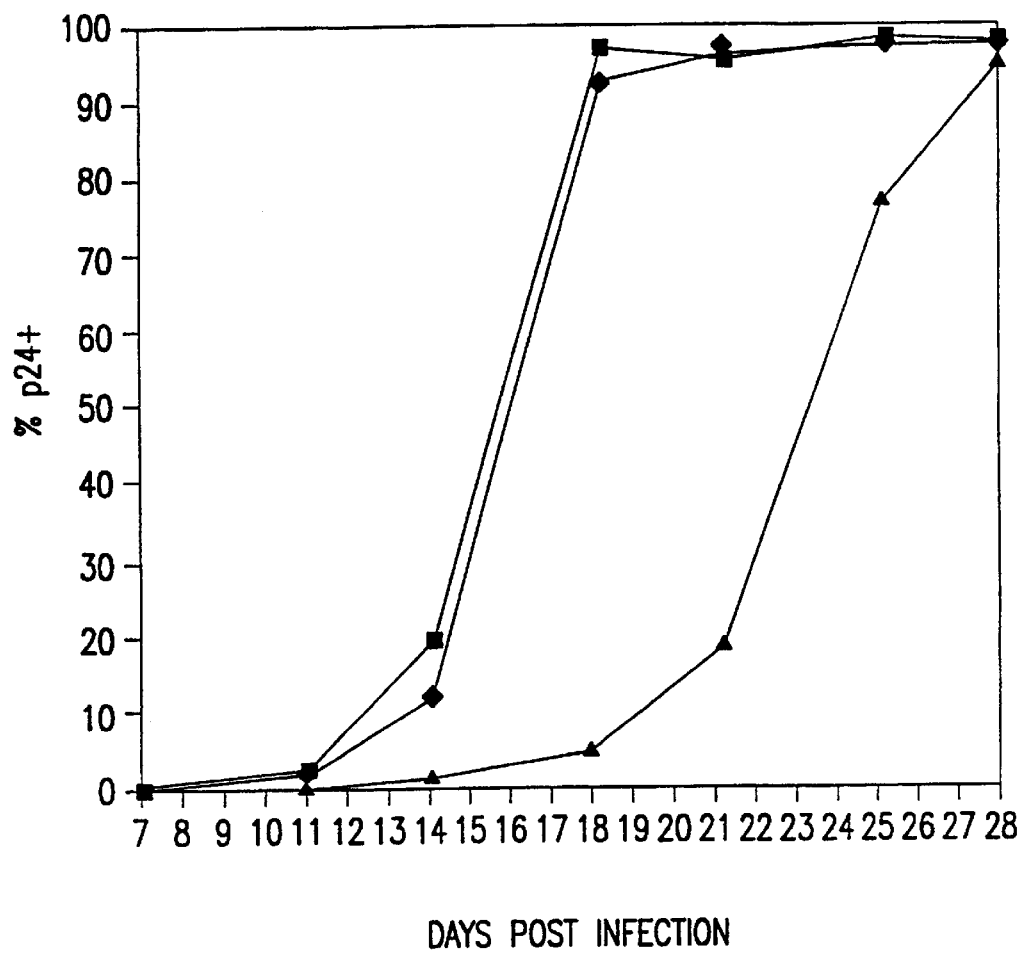

FIG. 17. Percentage of intracellular p24+ CEM-ss cells containing the IGX-004 constructs (the two opening reading frames are denoted as 1 and 3) after infection with HIV-1$_{SF2}$ at a TCID$_{50}$ of 500. CEM-ss cells ($10^6$) containing the IGX-004 constructs or 34 (plasmid DNA in LXSN) were harvested on the-indicated days post infection, stained with FITC-conjugated anti-p24 and analyzed by flow cytometry. Construct 3 represents the integrase reading frame, while construct 1 represents an alternative reading frame. Negative control (34), -♦-; construct 1, -■-; construct 3, -♦-.

Figure 18:
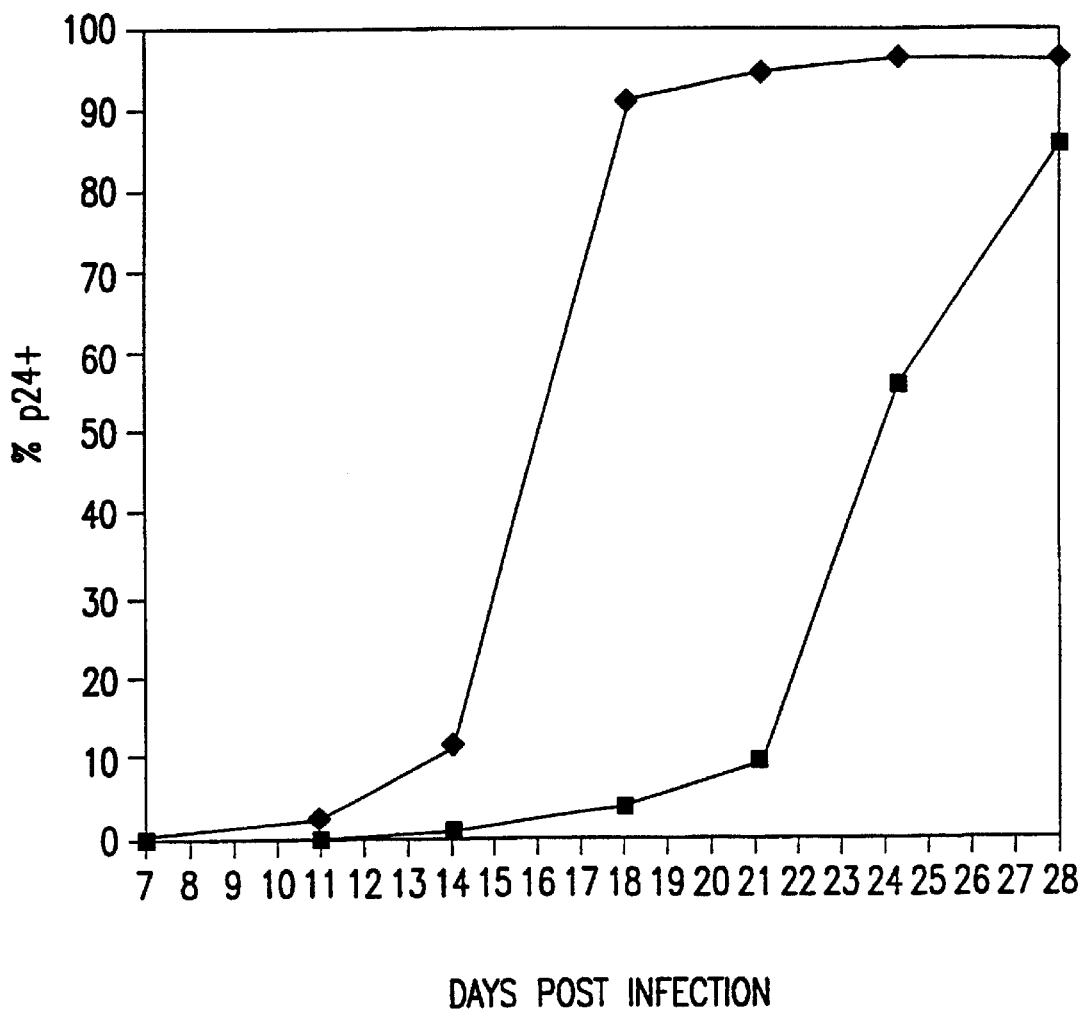

FIG. 18. Percentage of intracellular p24+ CEM-ss cells containing the IGX-009 sequence after infection with HIV-1$_{SF2}$ at a TCID$_{50}$ of 500. CEM-ss cells ($10^6$) containing the IGX-009 construct or 34 (plasmid DNA in LXSN) were harvested on the indicated days post infection, stained with FITC-conjugated anti-p24 and analyzed by flow cytometry. Negative control (34), -♦-; IGX-009, -■-.

5. DETAILED DESCRIPTION OF THE INVENTION

The present invention relates to specific HIV-derived polynucleotides identified by an improvement of the method disclosed by Roninson et al. in U.S. Pat. No. 5,217,889. More specifically, the improvement of the method includes the use of a cell line containing a latent and inducible HIV-1 provirus such as OM10.1. In addition, the improvement also encompasses the use of a marker associated with HIV infection such as CD4 to select for polynucleotides from an HIV-1 RFE library that effectively suppress HIV-1 infection. The GSE selected by this procedure are also able to protect uninfected cells from HIV infection.

FIG. 1 presents a schematic drawing of one specific method used to identify several GSE from a RFE library that prevent the induction of latent HIV-1. The method includes the steps of: 1) fragmenting the HIV-1 genome into 100–700 base pair (bp) fragments, 2) inserting the fragments into expression vectors such that the fragments are transcribed and translated to form an expression library; 3) transferring the expression library into a population of cells containing an inducible latent HIV-1 provirus or susceptible to HIV infection; 4) selecting a subpopulation of cells which contain a subset of the expression library enriched for HIV-1 GSE by monitoring the expression of a cellular or viral marker associated with HIV infection; and 5) recovering the GSE from the selected cell population. The method further includes repetition of the aforementioned steps with a secondary or tertiary library so that many rounds of successive selection can be performed. The selection of GSE can be performed by monitoring the continued expression of a cellular marker such as CD4 or the decreased expression of a viral marker such as p24 or gp120 using an antibody.

The invention is discussed in more detail in the subsections below, solely for purposes of description and not by way of limitation. For clarity of discussion, the specific procedures and methods described herein are exemplified using OM10.1 cells, CEM-ss cells, tumor necrosis factor-alpha (TNF-α), an anti-CD4 antibody, and an anti-p24 antibody, but they are merely illustrative for the practice of the invention. Analogous procedures and techniques are equally applicable to isolating GSE from different subtypes of HIV, utilizing any cell line containing an inducible latent provirus or any cell line or freshly isolated cell population susceptible to HIV infection, and any marker associated with HIV infection that can be easily assayed.

5.1. Preparation and Transfection of and HIV-1 GSE Library

An HIV RFE library can be constructed from the DNA of a plasmid or multiple plasmids that contain an HIV provirus insert. HIV proviral DNA is first treated with enzymes to produce randomly cleaved fragments. This can be conveniently performed by DNase I cleavage in the presence of Mn++ (Roninson et al., U.S. Pat. No. 5,217,889, column 5, lines 5–20). Thereafter, the randomly cleaved genomic DNA are size fractionated by gel electrophoresis. Fragments of between 100 and 700 bp are the preferred lengths for constructing RFE libraries. Single strand breaks of the size-selected fragments are repaired, e.g., by Klenow or T4 polymerase, and ligated with 5' and 3' adaptors.

The 5' and 3' adaptors are selected to have non-cohesive restriction sites so that each fragment can be inserted into an expression vector in an oriented fashion. Further, the 5' adaptor contains a start (ATG) codon to allow the translation of the fragments which contain an open reading frame in the correct phase.

After ligation with the adaptors the fragments are inserted into appropriate expression vectors. Any expression vector that results in efficient expression of the fragments in host cells can be used. In a preferred embodiment a viral based vector such as the retroviral vector LXSN is exemplified (Miller and Rosman, 1989, BioTechniques 7:980). Alternatively, adeno-associated virus vectors may also be used for this purpose.

When viral-based vectors are used, the ligated vectors are first transfected into a packaging cell line to produce viral particles. For retroviral vectors, any amphotropic packaging line such as PA317 (Miller and Buttimore, 1986, Mol. Cell. Biol. 6:2895–2902; ATCC CRL #9078) may be used to efficiently produce virus. In a preferred embodiment of the invention, the viral vector also contains a selectable gene, such as the neo$^r$ gene, that allows selective growth of the cells that contain the vector.

The number of independent clones present in each GSE expression library may vary. In a preferred embodiment, libraries of about $5 \times 10^4$ to $10^6$ independent clones may be used.

5.2. Selection of GSE in HIV-infected Cells

In a specific embodiment by way of example, OM10.1 cells are used to select for GSE, and they are maintained in conventional tissue culture as described in Butera (U.S. Pat. No. 5,256,534). The purpose of using OM10.1 cells for the selection of HIV-1 GSE is that they contain a latent HIV-1 provirus which is inducible by TNF-α. Other cell lines may be similarly engineered with an inducible HIV provirus. Examples of cell lines that are infected with latent HIV include, but are not limited to U1, U33, 8E5, ACH-2, LL58, THP/HIV and UHC4 (Bednarik and Folks, 1992, AIDS 6:3–16). A variety of agents have been shown to be capable of inducing latent HIV-infected cells, and these include TNF-α, TNF-β, interleukins-1, -2, -3, -4 and -6, granulocyte-macrophage colony stimulating factors, macrophage-colony stimulating factors, interferon-γ, transforming growth factor-β, PMA, retinoic acid and vitamin D3 (Poli and Fauci, 1992, AIDS Res. Human Retroviruses 9:191–197).

The HIV-infected cells may be transduced with the HIV-1 RFE library by any technique well known in the art that is appropriate to the vector system employed. In one embodiment of the invention, the viral vector also contains a selectable marker in addition to a random fragment of the HIV-1 genome. A suitable marker is the neo$^r$ gene, which permits selection by the drug G-418. In alternative embodiments the multiplicity of infection of the virions of the library is adjusted so that pre-selection for cells that are transduced by the vector is not needed.

In the case of OM10.1 cells, the transduced population is treated with 10 U/ml TNF-α for a period of 24–72 hours and preferably about 24 hours according to the method of Butera. The activation of the latent HIV-1 provirus in OM10.1 can be detected by the suppression of the cell surface CD4. It is believed that viral protein gp120 binds to CD4 in the cytoplasm, which prevents subsequent expression of CD4 on the cell surface. Clones that are resistant HIV replication continue to express cell surface CD4. Such clones can be selected by cell sorting using any conventional antibody staining technique for CD4 and a fluorescence activated cell sorter (FACS).

After selection for continued CD4 expression, the OM10.1cells harboring putative GSE and sorted after TNF-α induction are used to purify genomic DNA and the inserts amplified by the polymerase chain reaction (PCR). Optionally, the selected OM10.1 cells can be re-cultured under the selection conditions for the marker gene, e.g., in G-418, to ensure that the cells have retained the GSE derived from the HIV-1 RFE library.

The fraction of CD4$^+$ cells that have been transduced with an HIV-1 RFE library can be compared with cells transduced with an expression library consisting of the vector only. An increased relative difference between the HIV-1 RFE library and the control library can be found with each additional round of TNF-α induction. Thus, in the preferred embodiment of the invention there are at least two cycles of induction, selection and reculturing before the HIV-1 GSE are recovered from the cells for further characterization.

5.3. Recovery GSE from the Selected Cells

After selection, specific GSE sequences can be recovered from cells that continue to express CD4 following induction of the latent HIV provirus by TNF-α. The recovery may be performed by first expanding the population of selected cells in culture and preparing their genomic DNA. The HIV-1-associated GSE in this population are recovered by amplification in PCR using the primers according to the sequence of the linkers.

The recovered GSE can be introduced into an expression vector as discussed in Section 5.1, supra. The resultant HIV-1 GSE expression library is known as a secondary library. The secondary library may utilize the same or a different vector from that used for the construction of the primary library. The secondary library may be transduced into another cell population and the resultant population selected, recultured and processed as described herein.

Additionally, each individually recovered element can be inserted into cloning vectors for determining its specific nucleotide sequence, its orientation and the portion of HIV genome from which it is derived. Concurrently, the isolated GSE can be analyzed to determine their minimal core sequences and tested for their ability to protect previously uninfected cells from HIV infection.

In addition to the sequences depicted in FIGS. 4–11 (SEQ ID NOS:5–12), nucleotide sequences capable of hybridizing to these sequences or their complementary sequences under highly or less highly stringent hybridization conditions are well within the scope of the invention. Highly stringent hybridization conditions may be defined as hybridization to filter-bound DNA in 0.5 M NaHPO4, 7% sodium dodecyl sulfate (SDS), 1 mM EDTA at 65° C., followed by washing in 0.1×SSC/0.1% SDS at 68° C. (Ausubel F.M. et al., eds, 1989, Current Protocols in Molecular Biology, Vol. I, Green Publishing Associates, Inc., and John Wiley & Sons, Inc., N.Y. at p. 2.10.3). Less highly stringent conditions, such as moderately stringent conditions, may be defined as hybridizations carried out as described above, followed by washing in 0.2×SSC/0.1% SDS at 42° C. (Ausubel et al., 1989, supra).

5.4. Determination of Core Sequences of GSE

The present invention also includes methods for determining the core sequence of each GSE. This may be done by comparing overlapping sequences of independently derived GSE. Alternatively, GSE may be altered by additions, substitutions or deletions and assayed for retention of HIV-suppressive function. Alterations in the GSE sequences may be generated using a variety of chemical and enzymatic methods which are well known to those skilled in the art. For example, oligonucleotide-directed mutagenesis may be employed to alter the GSE sequence in a defined way and/or to introduce restriction sites in specific regions within the sequence. Additionally, deletion mutants may be generated using DNA nucleases such as Bal 31 or Exo III and S1 nuclease. Progressively larger deletions in the GSE sequences may be generated by incubating the DNA with nucleases for increased periods of time (See Ausubel, et al., 1989 Current Protocols for Molecular Biology, for a review of mutagenesis techniques).

The altered sequences may be evaluated for their ability to suppress expression of HIV proteins such as p24 in appropriate host cells. It is well within the scope of the present invention that any altered GSE sequences that retain their ability to suppress HIV infection may be incorporated into recombinant expression vectors for further use.

5.5. Protection of Uninfected Cells by GSE Against HIV-1 Infection

In order to confirm that the selected GSE can protect uninfected cells from HIV-1 infection, the GSE may be transferred into HIV susceptible host cells, followed by HIV infection. Protection experiments can be performed in any cell type that takes up the potential HIV-1 GSE and which is otherwise susceptible to HIV infection. In a preferred embodiment by way of example, the CEM-ss cell line is used (Foley et al., 1965, Cancer 18:522–29). The use of CEM-ss cells as targets for quantitative infectivity of HIV-1 has been described by Nara & Fischinger (1988, Nature 322:469–70). Other cell lines that are susceptible to HIV infection include, but are not limited to, HUT-78, H9, Jurkat E6-1, A3.01, U-937, AA-2, HeLa $CD4^+$ and C8166.

The test of the potential HIV-1 GSE can be performed using the same expression vector system as that employed in the RFE library transduction of cells during initial selection steps. In other embodiments, the vector system can be modified to achieve higher levels of expression, e.g., the linkers can be employed to introduce a leader sequence that increases the translational efficiency of the message. One such sequence is disclosed by Kozak, 1994, Biochemie 76:815–821.

Another way of testing the effectiveness of a GSE against HIV is to determine how rapidly HIV-1 variants develop that can negate the effects of the potential HIV-1 GSE. Such a test includes infection of a culture of susceptible cells such as CEM-ss cells at a low multiplicity of infection and repeatedly assaying the culture to determine whether and how quickly HIV-1 infection becomes widespread. The range of useful multiplicities of infection is between about 100 to 1000 tissue culture infectious units ($TCID_{50}$) per $10^6$ CEM-ss cells. The $TCID_{50}$ is determined by an endpoint method and is important for determining the input multiplicity of infection (moi).

A parameter that correlates with the development in the test culture of HIV-1 strains that are resistant to the effects of the potential HIV-1 GSE is the fraction of cells that are infected in the culture. This fraction can be determined by any means. Immunofluorescent staining with an antibody specific for the HIV-1 p24 antigen of fixed permeabilized cells is a convenient method for determining the fraction of cells that is infected. Commercially available reagents are suitable for performing such tests (Lee et al., 1994, J. Virol. 68:8254–8264).

In Section 6.2, infra, three GSE were tested for their ability to protect CEM-ss cells from infection with HIV-1 strains $SF_2$ and $SF_{33}$. Uninfected cells were transduced with a LXSN construct containing either an irrelevant DNA or a GSE sequence. Non-transduced cells were eliminated by exposure to the selection agent, G-418. The percentage of $p24^+$ cells was determined at specific time points post infection. The results demonstrate that three out of three GSE tested are able to protect a productive HIV-1 infection in susceptible host cells.

5.6. Uses of GSE to Suppress HIV-1 Infection

Another aspect of the present invention is to use the isolated GSE against HIV infection prophylactically and therapeutically. In this connection, GSE operably linked to a regulatory sequence such as a promoter that controls its expression may be transferred in vitro into any HIV-susceptible host cells or hematopoietic stem cells such as $CD34^+$ cells obtained from bone marrow or mobilized peripheral blood, by any DNA transfer techniques well known in the art such as electroporation, transfection or transduction, followed by transplantation of the cells into a recipient. When the GSE-containing cells differentiate in vivo, the progeny cells express the GSE and become resistant to HIV.

Alternatively, GSE may be directly administered in vivo using a gene therapy expression vector. In particular, anti-HIV GSE can be delivered or transferred into $CD4^+$ T cells in both HIV-infected or uninfected individuals to protect against development of HIV infection. GSE can also be transferred into stromal cells, including macrophages.

Expression vectors derived from viruses such as retroviruses, adeno-associated virus, herpes viruses, or bovine papilloma virus may be used for delivery of recombinant GSE into the targeted cell population. Methods which are well known to those skilled in the art can be used to construct recombinant viral vectors containing a GSE sequence operably linked to a promoter that controls its expression (Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). In a specific embodiment by way of example, GSE sequences were inserted into a retroviral vector. In cases where an adenovirus is used as an expression vector, a GSE sequence may be ligated to an adenovirus transcription-translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing GSE in infected hosts (Logan & Shenk, 1984, Proc. Natl. Acad. Sci. USA 81:3655–3659).

Alternatively, recombinant GSE nucleic acid molecules can be reconstituted into liposomes for delivery to target cells. Liposomes are spherical lipid bilayers with aqueous interiors. All molecules that are present in an aqueous solution at the time of liposome formation (in this case, oligonucleotides) are incorporated into this aqueous interior. The liposomal contents are both protected from the external microenvironment and, because liposomes fuse with cell membranes, are efficiently delivered into the cell cytoplasm, obviating the need to neutralize the polynucleotides' negative charge.

Specific initiation signals may also be required for efficient translation of inserted GSE sequences. Exogenous transcriptional control signals, including the ATG initiation codon, must be provided. Furthermore, the initiation codon must be in phase with the reading frame of the GSE sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153: 516–544).

The isolated GSE sequences suppress HIV activity by either encoding protein or RNA products. The present invention encompasses any such protein product, including fusion proteins, leader peptides and localization signals. In addition, anti-sense RNA, DNA molecules and ribozymes that function to inhibit HIV infection are also within the scope of the invention. Anti-sense RNA and DNA molecules act to directly block the translation of mRNA by binding to targeted mRNA and preventing protein translation. GSE may be represented by structural RNAs which act as decoys.

Some GSE may also form triplexes. Oligodeoxyribonucleotides can form sequence-specific triple helices by hydrogen bonding to specific complementary sequences in duplexed DNA. Formation of specific triple helices may selectively inhibit the replication and/or gene expression of targeted genes by prohibiting the specific binding of functional trans-acting factors.

Polynucleotides to be used in triplex helix formation should be single stranded and composed of deoxynucleotides. The base composition of these polynucleotides must be designed to promote triple helix formation via Hoogsteen base pairing rules, which generally require sizeable stretches of either purines or pyrimidines to be present on one strand of a duplex. Polynucleotide sequences may be pyrimidine-based, which will result in TAT and CGC triplets across the three associated strands of the resulting triple helix. The pyrimidine-rich polynucleotides provide base complementarity to a purine-rich region of a single-strand of the duplex in a parallel orientation to that strand. In addition, polynucleotides may be chosen that are purine-rich, for example, containing a stretch of G residues. These polynucleotides will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" oligonucleotide. Switchback oligonucleotides are synthesized in an alternating 5'–3', 3'–5' manner, such that they base pair with first one strand of a duplex and then the other, eliminating the necessity for a sizeable stretch of either purines or pyrimidines to be present on one strand of a duplex.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of HIV RNA sequences. GSE represented by antisense RNA showing high affinity binding to target sequences can also be used as ribozymes by addition of enzymatically active sequences known to those skilled in the art.

Both anti-sense RNA and DNA molecules, and ribozymes of the invention may be prepared by any method known in the art. These include techniques for chemically synthesizing oligodeoxyribonucleotides well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into host cells.

Various modifications to the nucleic acid molecules may be introduced as a means of increasing intracellular stability and half-life. Possible modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Methods for introducing polynucleotides into cells or tissues include the insertion of naked polynucleotide, i.e., by injection into tissue, the introduction of a GSE in a cell ex vivo, i.e., for use in autologous cell therapy, the use of a vector such as a virus, retrovirus, phage or plasmid, etc. or techniques such as electroporation which may be used in vivo or ex vivo.

The GSE may be formulated and administered through a variety of means, including systemic, localized, or topical administration. Techniques for formulation and administration may be found in "Remington's Pharmaceutical Sciences," Mack Publishing Co., Easton, Pa., latest edition. The mode of administration may be selected to maximize delivery to a desired target site in the body.

For systemic administration, route of injection includes, intramuscular, intravenous, intraperitoneal, and subcutaneous. The polynucleotides of interest are formulated in aqueous solutions, preferably in physiologically compatible buffers such as Hanks's solution, Ringer's solution, or physiological saline buffer. In addition, the polynucleotides may be formulated in solid or lyophilized form, then redissolved or suspended immediately prior to use.

6. EXAMPLE: ISOLATION AND IDENTIFICATION OF GSE AGAINST HIV-1

6.1. Materials and Methods 6.1.1. Construction of RFE Library

Cloned genomic DNA, plasmids pBENN6 (Cat. No. 343) and pBENN7 (Cat. No. 342) or pBH10 (Cat. No. 90) from National Institutes of Health (NIH) AIDS Research and Reference Reagent Program, which contained the entire HIV-1 genome was partially digested with DNAseI in the presence of manganese (Sambrook et al., 1989, Molecular Cloning A Laboratory Manual, Cold Spring Harbor Laboratory, N.Y.). Under these conditions, DNAseI is known to produce mostly double-stranded breaks. The resulting fragments were repaired with the Klenow fragment of DNA polymerase I and T4 polymerase and ligated to synthetic double-stranded adaptors. The 5' adaptor (SEQ ID NOS:1 and 2):

5'-CTCGGAATTCAAGCTTATGGATGGATG

3' CCTTAAGTTCGAATACCTACCTAC-5'

The 3' adaptor (SEQ ID NOS:3 and 4):

5'TGAGTGAGTGAATCGATGGATCCGTCT

ACTCACTCACTTAGCTACCTAGGCAGATCCT-5'

Thereafter, the mixture was digested with BamHI and EcoRI, column purified and ligated to the retroviral vector LXSN (Miller and Rosman, 1989, BioTechniques 7:980–990) cut with EcoRI and BamHI. The ligation mixture was transformed into E. coli. The total plasmid was purified from ~100,000 recombinant clones. The size distribution of the cloned fragments was tested by PCR amplification using primers derived from the vector sequences adjacent to the adaptors.

6.1.2. Cell Lines and Reagents

The OM10.1 cells are available from the American Type Culture Collection, Rockville, Md. as CRL 10850 (Butera, U.S. Pat. No. 5,256,534). The CEM-ss cells are available from the NIH AIDS Research and Reference Reagent Program as Cat. No. 776. HIV-1$_{SF2}$ is available from NIH AIDS Research and Reference Reagent Program as Cat. No. 275.

The anti-CD4 (Q4120PE) and anti-p24 (KC-57 FITC) antibodies were purchased from Sigma and Coulter, respectively. TNF-α was obtained from Boehringer Mannheim. G418 was purchased from Gibco/BRL as Geneticin.

6.1.3. Transduction and Selection of GSE

The plasmid DNA prepared according to the method of Section 6.1.1. supra, was transfected into the packaging cell line, PA317 (ATCC CRL #9078), and converted into retrovirus for infection of OM10.1 cells. After G418 selection, the OM10.1 cells harboring the entire RFE library were induced with 10 U/ml of TNF-α at 37° C. and, 24 hours later, were stained with an antibody and sorted for CD4 expression. The CD4$^+$ cells were cultured, expanded in number, and genomic DNA from the CD4$^+$ cells was purified and used for PCR amplification of inserts with the vector-derived primers. The amplified mixture was digested with EcoRI and BamHI and cloned back into the LXSN vector. The selection was repeated.

6.1.4. Immunofluorescence and Flow Cytometry

For the selection of CD4$^+$ cells, 10$^7$ cells were washed twice with Assay Buffer (500 ml PBS, 1 ml of 0.5 mM of EDTA at pH 8, 0.5 ml of 10% sodium azide and 10 ml of fetal bovine serum), and resuspended in 500 μl PBS to which 50 μl of anti-CD4 antibody (Q4120 PE, Sigma) was added. After incubation at 4° C. for 30 min., 5 ml of Assay Buffer was added and the cells centrifuged at 1200 rpm for 4 min. The cells were washed twice with Assay Buffer before sorting by FACS. The aforementioned procedure was performed under sterile conditions.

In order to determine p24 expression in HIV-infected cells, the cells were first washed twice with Assay Buffer. About 10$^6$ cells were suspended in 100 μl Assay Buffer, mixed with 2 ml of Ortho PermeaFix Solution (Ortho Diagnostics), and incubated for 40 min. at room temperature. After centrifugation at 1200 rpm for 4 min. at 4° C., the cells were resuspended in 2 ml Wash Buffer (500 ml PBS, 25 ml fetal bovine serum, 1.5% bovine serum albumin and 0.0055% EDTA) for 10 min. at room temperature. After centrifugation, the cells were resuspended in 50 μl Wash Buffer and mixed with 1:500 dilution of an IgG$_{2a}$ antibody for 20 min. at 4° C., followed by incubation with 5–10 μl of anti-p24 antibody (KC57-FITC, Coulter) for 30 min. at 4° C. The cells were then washed twice with Wash Buffer and analyzed by flow cytometry.

6.1.5. Recovery of GSE and Sequence Analysis

Genomic DNA was isolated from the selected population of OM10.1 cells harboring putative GSE by resuspending the cell pellet in 0.1% Triton X-100, 20 μg/ml proteinase K in 1×PCR buffer, incubating at 55° C. for 1 hour, and boiling for 10 minutes. Genomic DNA was used for PCR amplification using vector-derived primers, cloned into the LXSN vector, and transformed into E. coli using techniques well known in the art. Individual plasmids were purified from E. coli clones using QIAGEN plasmid kits. Inserts were sequenced by the dideoxy procedure (AutoRead Sequencing Kit, Pharmacia Biotech) and run on a Pharmacia LKB A.L.F. DNA sequencer. Sequences were analyzed using the DNAS-TAR program.

6.2. Results

HIV-1 GSE were isolated and identified according to the general scheme of FIG. 1. An HIV-1 RFE library was constructed from plasmids containing the entire genome of the virus. Following transfection of the entire library into a packaging cell line, virus was transferred into OM10.1 cells by co-cultivation. The virally-transduced cells were selected in culture medium containing G-418 to ensure the retention of the viral vector.

When the transduced OM10.1 cells were treated with TNF-α and stained with an antibody specific for the cell surface molecule CD4, a rapid loss of CD4 expression was observed (FIG. 2). In contrast, the vast majority of the uninduced OM10.1 cells retained CD4 expression. It is believed that activation of the latent virus in OM10.1 cells by TNF-α led to the production of viral protein gp120, which bound to cytoplasmic CD4, thereby preventing its cell surface translocation. A diminution of CD4$^+$ OM10.1 cells also correlated with an increased production of viral protein p24 in the cells following TNF-α induction (FIG. 3).

The small number of residual CD4$^+$ cells were then stained with an anti-CD4 antibody and sorted by FACS. After the cells were expanded in culture, the individual GSE polynucleotides were recovered by PCR amplification and their nucleotide sequences determined. FIGS. 4–9 present the nucleotide sequences of six polynucleotides (IGX-004, IGX-024, IGX-042, IGX-009, IGX-005, IGX-230) corresponding to GSE in the sense orientation, whereas FIGS. 10 and 11 present the nucleotide sequences of two GSE (IGX-003 and IGX-170) in the antisense orientation. FIG. 12 shows the location of the isolated GSE on the HIV-1 genome. These GSE are distributed throughout different regions of the genome. For example, the IGX-004 GSE (SEQ ID NO:5) is located within the integrase gene, the IGX-009 GSE (SEQ ID NO:8) is located within the Nef gene, and the IGX-230 GSE (SEQ ID NO:10) overlaps the Rev and Tat genes.

Three GSE, IGX-230, IGX-004 and IGX-009, were further tested for their ability to protect uninfected human T cells from a productive HIV-1 infection. The plasmids containing each of these sequences were transduced into CEM-ss cells followed by G418 selection. The Rev transdominant mutant, RevM10 (Malin et al., 1989, Cell 58:205), and a LXSN vector containing an irrelevant piece of plasmid DNA (34) were used as controls. The G418 resistant cells were 99% CD4$^+$, and were then infected with low titers (TCID$_{50}$ of 200) of HIV-1$_{SF2}$ and high titers (TCID$_{50}$ of 1000) HIV-1$_{SF33}$. The cells were removed at 21, 28 and 35 days after infection with the low titers and at 9 days after infection with the high titers, and stained with a fluorescinated-anti-p24 antibody as an indicator of HIV infection.

FIG. 13 shows that the IGX-004 sequence was able to suppress infection with HIV-1$_{SF2}$, as evidenced by the low percentage of p24$^+$ cells over one month after infection. Only 1%, 3% and 44% of the cells transduced with the IGX-004 sequence were positive for p24 expression on days 21, 28 and 35, respectively. For negative control (34), 64% of the cells were positive for p24 at day 21, and 99% of the cells became p24$^+$ cells by day 28. Transduction of RevM10 led to 8% p24$^+$ cells on day 21, 87% p24$^+$ cells on day 28 and 95% p24$^+$ cells on day 35. A pattern similar to RevM10 was seen for the IGX-230 sequence with 4% of p24$^+$ cells on day 21, 80% on day 28 and 92% on day 35. Thus, the IGX-230 sequence produced an intermediate suppressive effect between that of negative control and IGX-004 sequences.

Additionally, the percentage of intracellular p24$^+$ cells was also determined at 9 days after infection of CEM-ss cells with high titers of HIV-1$_{SF33}$ (FIG. 14). Again, the IGX-004 sequence was most effective at suppressing p24 expression at 29%, whereas the negative control (34) and the IGX-230 sequences produced 97% and 45% p24$^+$ cells, respectively.

FIG. 12 shows that the GSE IGX-230 encompasses portions of both the Rev and Tat genes. In order to determine the functional reading frame of IGX-230, constructs representing all three potential reading frames were made and transferred into OM10.1 cells. The constructs contained sequences in three open reading frames using 5' adaptors that contained the Kozak sequence (Kozak, 1994, Biochemie 76:815–821). After TNF-α induction, the cells were analyzed 24 hours later for CD4 and p24 expression. Interestingly, all three open reading frames of IGX-230 suppressed latent HIV activation, as measured by the continued expression of CD4 (FIG. 15). CD4 expression directly correlated with a decrease of p24 levels in the cells. Furthermore, when the constructs containing the three open reading frames were transferred into CEM-ss cells following infection with HIV-1$_{SF2}$ they were also able to suppress the expression of p24 over time (FIG. 16). These results suggest that IGX-230 may function as a structural RNA rather than as a coding sequence for a protein product.

The same experiment was performed with two constructs of the GSE IGX-004 which mapped within the HIV-1 integrase gene. FIG. 17 demonstrates that the construct corresponding to the integrase reading frame strongly suppressed the levels of p24 in CEM-ss cells after HIV-1 infection for over three weeks. In contrast, the construct representing an alternative reading frame was not active.

A third GSE, IGX-009, which mapped within the Nef gene was also able to sustain CD4 expression and suppress p24 levels in OM10.1 cells after TNF-α induction. In addition, the IGX-009 sequence protected CEM-ss cells from HIV-1$_{SF2}$ infection, as shown by its ability to suppress intracellular p24 levels as compared to a control sequence (FIG. 18).

In conclusion, a large number of GSE have been isolated from the HIV-1 genome based on their ability to maintain CD4 expression in OM10.1 cells after activation of latent HIV by induction with TNF-α. The isolated GSE contain nucleotide sequences in both sense and anti-sense orientations, and are mapped to different regions of the HIV-1 genome. Several elements corresponding to portions of the integrase, Nef and Rev/Tat genes are able to suppress HIV-1 infection of T cells by reducing p24 levels in infected cells. Such polynucleotides are useful in protecting the infection by and/or suppressing the replication of HIV-1 in human host cells.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A human immunodeficiency virus type 1 (HIV-1) genetic suppressor element (GSE) consisting of SEQ ID No.: 5 operably linked to a promoter, wherein said GSE is capable of inhibiting HIV-1 viral activation when expressed in a latently infected cell.

2. A human immunodeficiency virus type 1 (HIV-1) genetic suppressor element (GSE) consisting of SEQ ID No.: 6 operably linked to a promoter, wherein said GSE is capable of inhibiting HIV-1 viral activation when expressed in a latently infected cell.

3. A human immunodeficiency virus type 1 (HIV-1) genetic suppressor element (GSE) consisting of SEQ ID No.: 7 operably linked to a promoter, wherein said GSE is capable of inhibiting HIV-1 viral activation when expressed in a latently infected cell.

4. A human immunodeficiency virus type 1 (HIV-1) genetic suppressor element (GSE) consisting of SEQ ID No.: 8 operably linked to a promoter, wherein said GSE is capable of inhibiting HIV-1 viral activation when expressed in a latently infected cell.

5. A human immunodeficiency virus type 1 (HIV-1) genetic suppressor element (GSE) consisting of SEQ ID No.: 9 operably linked to a promoter, wherein said GSE is capable of inhibiting HIV-1 viral activation when expressed in a latently infected cell.

6. A human immunodeficiency virus type 1 (HIV-1) genetic suppressor element (GSE) consisting of SEQ ID No.: 10 operably linked to a promoter, wherein said GSE is capable of inhibiting HIV-1 viral activation when expressed in a latently infected cell.

7. A human immunodeficiency virus type 1 (HIV-1) genetic suppressor element (GSE) consisting of SEQ ID No.: 11 operably linked to a promoter, wherein raid GSE is capable of inhibiting HIV-1 viral activation when expressed in a latently infected cell.

8. A human immunodeficiency virus type 1 (HIV-1) genetic suppressor element (GSE) consisting of SEQ ID No.: 12 operably linked to a promoter, wherein said GSE is capable of inhibiting HIV-1 viral activation when expressed in a latently infected cell.

* * * * *